United States Patent [19]

Nakada et al.

[11] Patent Number: 5,763,703
[45] Date of Patent: Jun. 9, 1998

[54] MANUFACTURING METHOD FOR HEXAFLUOROCYLOBUTENE AND HEXAFLUOROCYCLOBUTANE

[75] Inventors: Tatsuo Nakada; Hirokazu Aoyama; Akinori Yamamoto, all of Settsu, Japan

[73] Assignee: Daikin Industries Ltd., Osaka, Japan

[21] Appl. No.: 600,920

[22] PCT Filed: Aug. 3, 1994

[86] PCT No.: PCT/JP94/01285

§ 371 Date: Feb. 26, 1996

§ 102(e) Date: Feb. 26, 1996

[87] PCT Pub. No.: WO95/06022

PCT Pub. Date: Mar. 2, 1995

[30] Foreign Application Priority Data

Aug. 27, 1993 [JP] Japan ................. 5-235531
Jan. 10, 1994 [JP] Japan ................. 6-012209

[51] Int. Cl.$^6$ ............... C07C 17/00; C07C 17/25; C07C 19/08
[52] U.S. Cl. .................. 570/155; 570/132; 570/156
[58] Field of Search ............... 570/132, 155, 570/156

[56] References Cited

U.S. PATENT DOCUMENTS

| | | | |
|---|---|---|---|
| 2,436,142 | 2/1948 | Harmon | 570/132 |
| 2,590,019 | 3/1952 | Kropa et al. | 570/132 |
| 3,996,299 | 12/1976 | Fozzard | 570/155 |
| 4,954,666 | 9/1990 | Bielefeldt et al. | 570/132 |
| 5,068,473 | 11/1991 | Kellner et al. | 570/176 |
| 5,416,246 | 5/1995 | Krespan et al. | 570/151 |
| 5,523,497 | 6/1996 | Lui et al. | 570/155 |

*Primary Examiner*—Deborah Lambkin
*Attorney, Agent, or Firm*—Armstrong, Westerman, Hattori, McLeland & Naughton

[57] ABSTRACT

Manufacturing method for hexafluorocyclobutene in which 1,2-dichlorohexafluorocyclobutane is dechlorinated using hydrogen in the presence of a metal oxide and/or silicon oxide catalyst. Manufacturing method for (Z)-1,2,3,3,4,4-hexafluorocyclobutane which carries out the hydrogen-adding reaction (hydrogen reduction) of the raw material, 1,2-dichlorohexafluorocyclobutane, in the presence of a rhodium catalyst, or which carries out vapor-phase hydrogen reduction of hexafluorocyclobutene in the presence of a palladium catalyst.

Using this manufacturing method, hexafluorocyclobutene can easily be derived in a single step with high selectivity from 1,2-dichlorohexafluorocyclobutane which can be obtained readily and at a low cost. This method also produces a high yield of (Z)-1,2,3,3,4,4-hexafluorocyclobutane.

20 Claims, No Drawings

MANUFACTURING METHOD FOR HEXAFLUOROCYLOBUTENE AND HEXAFLUOROCYCLOBUTANE

This application is a 371 of PCT/JP94/01285, Aug. 3, 1994.

INDUSTRIAL USES

This invention is concerned with the method of manufacturing hexafluorocyclobutene, a useful compound that can be employed not only as a raw material for detergents and HFC foaming agents which will not deplete the ozone layer, but also a raw material for various resins and serve as an intermediate for medicinal drugs and agricultural chemicals. This invention can also be applied to the method of manufacturing (Z)-1,2,3,3,4,4-hexafluorocyclobutane, a useful compound that can be employed as an alternate to CFCs and HCFCs presently being used as refrigerants, blowing agents and detergents.

CONVENTIONAL TECHNOLOGIES

The method of carrying out the reaction of zinc with 1,2-dichlorohexafluorocyclobutane in alcohol to obtain hexafluorocyclobutene is well known (G. Fuller and J. C. Tatlow, J. Chem Soc., 3198 (1961)).

The reaction, however, requires a large quantity of solvent and also involves enormous costs for processing zinc chloride produced by the reaction. Therefore, the process cannot be considered effective for industrial use.

The method for reducing 1,2-dichlorohexafluorocyclobutane using lithium aluminum hydride (LiAlH$_4$), is known as the (Z)-1,2,3,3,4,4-hexafluorocyclobutane manufacturing method (also described in the above-mentioned document).

However, the yield of (Z)-1,2,3,3,4,4-hexafluorocyclobutane using this common method is low as being a 30% yield. The method also produces a large quantity of the geometrical isomer of the target compound, (E)-1,2,3,3,4,4-hexafluorocyclobutane, as a by-product. Therefore, this method is not suitable for industrial use. In this paper, (Z) refers to "Zusammen" which corresponds to the "cis" form; and (E) refers to "Entgegen" which corresponds to the "trans" form.

PURPOSES OF THE INVENTION

One purpose of this invention is to provide an easy and inexpensive method with high selectivity of hexafluorocyclobutene from 1,2-dichlorohexafluorocyclobutane.

Another purpose of the invention is to provide a high-yield method for manufacturing (Z)-1,2,3,3,4,4-hexafluorocyclobutane employing the hexafluorocyclobutene reduction reaction.

An additional purpose of this invention is to provide a high-yield method for manufacturing (Z)-1,2,3,3,4,4-hexafluorocyclobutane employing the 1,2-dichlorohexafluorocyclobutane reduction reaction.

CONSTRUCTION OF THE INVENTION

The inventors have conducted a thorough study of the processes for the efficient, low-cost manufacturing of hexafluorocyclobutene. As a result of the study, the inventors have perfected a process for high-selectively manufacturing hexafluorocyclobutene from 1,2-dichlorohexafluorocyclobutane available at low cost.

The invention is concerned with the method of manufacturing hexafluorocyclobutene, an intermediate for synthesis of (Z)-1,2,3,3,4,4-hexafluorocyclobutane, by dechlorinating 1,2-dichlorohexafluorocyclobutane using hydrogen in the presence of a catalyst consisting of metal oxide and/or silicon oxide, the metal oxide comprising at least one or plural kinds of metal selected from iron, chromium, cobalt, copper, nickel and manganese.

In the manufacturing process carried out according to the invention, the raw material, 1,2-dichlorohexafluorocyclobutane, is easily available by dimerizing 1,2,2-trifluoro-1-chloroethylene.

In addition, the metal oxide used as a catalyst in the reductive dehalogenation (dechlorination) of 1,2-dichlorohexafluorocyclobutane, can be obtained by calcinating the metal hydroxide sediment produced by the conventional method in which an alkali such as ammonia solution or alkaline metal hydroxide is added to chloride, sulfate, or nitrate solution of Cr, Fe, Co, Cu, Ni or Mn. Each of the metal oxides can be used alone. Moreover, compound oxide or mixed oxide of multiple metals selected from those above mentioned can be used as a catalyst for the reaction.

The catalyst can be granulated or compressed into a pellet shape. The oxide can be supported on a suitable carrier which is not directly involved in the reaction and made of one or more materials such as active carbon, alumina, aluminum fluoride and/or calcium fluoride. There is no problem even if the valence of the metal consisting catalyst is zero when they have been reduced by hydrogen during the pre-processing or reaction.

Commercially-available granulated, globular, or powdered silicon dioxide can also be used as the silicon oxide catalyst. For instance, "CARiACT" manufactured by Fuji Davison Co., Ltd., "Silbead" made by Mizusawa Chemical Industry Co., Ltd., or "M.S. GEL SIL", made by Asahi Glass Co., Ltd., can be used as the catalyst after crushing these compounds or compressing them into a pellet shape as occasion demands.

There is no problem whatsoever if the above-mentioned metal oxides are supported on a carrier made of silica gel, typically silicon oxide.

In addition, the reaction can be carried out when hydrogen use not less than one molar excess (at least a stoichiometric amount) of the raw material, but for practical use, it is desirable to carry out the reaction when hydrogen use is not less than one and a half molar excess. A large excess of hydrogen also shortens the contact time and decreases the conversion. In practical use, the molar ratio of hydrogen to the raw material is recommended from double to quintuple.

For the reductive dehalogenation, the reaction temperature can be selected within the range of 200° to 500° C. according to the activity of the each catalyst. As is generally known, the reaction rate increases as the reaction temperature rises. Therefore, a high reaction temperature is necessary for a catalyst with low activity. When the reaction temperature exceeds 500° C., however, by-products such as acyclic 2-carbon compounds increase due to cleavage in the carbon-carbon bond which cause to lower selectivity making it desirable to carry out the reaction at a temperature below 500° C.

The contact time can be adjusted to set appropriate conversion according to the activity of employed catalyst and the reaction temperature. Generally, when the catalyst activity is low, the appropriate conversion can be set by prolonging the contact time.

After thorough review of the method for manufacturing (Z)-1,2,3,3,4,4-hexafluorocyclobutane, the inventors perfected their invention after discovering that the targeted substance can be obtained with high selectivity when the hydrogen reduction of the raw material, hexafluorocyclobutene, is performed in the presence of a palladium catalyst.

Namely, this invention is a method of manufacturing (Z)-1,2,3,3,4,4-hexafluorocyclobutane by dechlorinating 1,2-dichlorohexafluorocyclobutane using hydrogen to obtain hexafluorocyclobutene in the presence of a catalyst consisting of metal oxide and/or silicon oxide, the metal oxide comprising at least one or plural kinds of metal selected from iron, chromium, cobalt, copper, nickel and manganese, and by performing hydrogen reduction of the hexafluorocyclobutene using a vapor-phase method under conditions in which a palladium catalyst is present.

Utilizing this invention, either the fixed-bed vapor-phase reaction or the fluidized bed vapor-phase reaction can be applied as a method of vapor-phase reaction in the manufacturing method, just as in the above-mentioned hexafluorocyclobutene manufacturing method.

The palladium catalyst is preferable to be supported by a carrier consisting of one or more of the substances selected from active carbon, alumina, silica gel, titanium oxide, and/or zirconia.

The carrier particle size has almost no effect on the reaction, but a size of 0.1–100 mm is desirable and appropriate. A wide range of supporting concentration, from 0.05–10%, can also be used, although usually a carrier with a supporting concentration of 0.5–5% is recommended. The values can be adopted for the above-mentioned hexafluorocyclobutene manufacturing method utilizing this invention.

A reaction temperature of 20°–300° C. is normally used, and 50°–150° C. is desirable.

The ratio of hydrogen to the raw material can be substantially changed in the hexafluorocyclobutene hydrogen reduction reaction, and at least a stoichiometric quantity of hydrogen can be used. Generally, though, hydrogenation is carried out using an amount of hydrogen which is 2–5 times its stoichiometric quantity. Quite a large quantity of hydrogen, beyond its stoichiometric quantity relative to the total mol of the raw material, for instance 10 mol or more of hydrogen, can be utilized.

There is no particular limit on the pressure that can be used for the reaction which can be carried out under pressurized, reduced or normal pressure conditions. However, the complicated apparatus is needed under reduced pressure conditions. Therefore, it is desirable to carry out the reaction under either pressurized or normal pressure conditions. A contact time of 0.1–300 seconds, in particular 1–30 seconds, is recommended. These conditions can be adopted for the above-mentioned hexafluorocyclobutene manufacturing method utilizing this invention.

The raw material hexafluorocyclobutene can be obtained by the above-mentioned method (the method of dechlorinating 1,2-dichlorohexafluorocyclobutane using hydrogen in the presence of a catalyst consisting of metal oxide and/or silicon oxide) in the (Z)-1,2,3,3,4,4-hexafluorocyclobutane manufacturing method utilizing this invention.

Moreover, the 1 2-dichlorohexafluorocyclobutane used to manufacture the hexafluorocyclobutene can be obtained by the dimerization reaction of 1,2,2-trifluoro-1-chloroethylene.

As a result of further thorough study of the manufacturing methods of (Z)-1,2,3,3,4,4-hexafluorocyclobutane, the inventors have found that the targeted substance can be obtained with a high yield and high selectivity when the hydrogen reduction of the raw material, 1,2-dichlorohexafluorocyclobutane, is carried out in the presence of a rhodium catalyst. When utilizing this method, (E)-1,2,3,3,4,4-hexafluorocyclobutane, the geometrical isomer of the target substance, is not produced.

In other words, the essential point of this invention is that it is a method of manufacturing a high yield of (Z)-1,2,3,3,4,4-hexafluorocyclobutane by a reaction of adding hydrogen to the raw material, 1,2-dichlorohexafluorocyclobutane; in particular, using hydrogen in an amount of equivalent to double the stoichiometric quantity of the raw material at a temperature of 150°–300° C. in the presence of a rhodium catalyst.

Palladium, platinum, rhodium, and Raney nickel, etc., are well-known as catalysts for the hydrogenolysis of halides. When the hydrogen reduction of 1,2-dichlorohexafluorocyclobutane is performed using a palladium catalyst (comparison example 1, below) or a platinum catalyst (comparison example 2, below), not only the raw-material conversion is low, but also (E)-1,2,3,3,4,4-hexafluorocyclobutane, the geometrical isomer of (Z)-1,2,3,3,4,4-hexafluorocyclobutane, is produced and the selectivity decreases.

In contrast, using a rhodium catalyst, the raw-material conversion is extremely high, and there is no or a little production of (E)-1,2,3,3,4,4-hexafluorocyclobutane, the geometrical isomer of (Z)-1,2,3,3,4,4-hexafluorocyclobutane. The inventors have clarified that (Z)-1,2,3,3,4,4-hexafluorocyclobutane, the target substance, can be obtained with high selectivity.

A catalyst carrier can be used that consists of one or more substances selected from common active carbon, alumina, silica and/or zirconia substances. Active carbon is the most desirable and highest target-substance selectivity can be obtained.

Either the fixed-bed vapor-phase reaction method or fluidized bed vapor-phase reaction method can be used as a method of vapor-phase reaction.

The particle size of the carrier has a few influence on the reaction, although the size of 0.1–10 mm is appropriate and desirable.

A wide range of supporting concentration from 0.05–10% can be applied, but usually a carrier with a supporting concentration of 0.5–5% is recommended.

The reaction temperature is normally 150°–300° C., and the desirable reaction temperature is 175°–250° C. When the reaction temperature is lower than 150° C., the selectivity is high, but the conversion is low. Moreover, if the reaction temperature exceeds 300° C., large quantities of by-products are produced.

In the above-mentioned 1,2-dichlorohexafluorocyclobutane hydrogen reduction reaction, when the quantity of hydrogen is more than the stoichiometric quantity of the raw material, 1,2-dichlorohexafluorocyclobutane, the ratio of hydrogen to the raw material can be drastically changed. However, the hydrogenation is usually carried out using hydrogen in an amount of 2–10 times, in particular 2–4 times, the stoichiometric quantity. A quantity of hydrogen considerably more than the stoichiometric quantity relative to the total molar quantity of the starting material can be used, for instance 10 mol or more of hydrogen, and the excess hydrogen can be recovered and reused.

There is no particular limit for reaction pressure. The reaction can be carried out under pressurized, reduced or normal pressure conditions, although complicated apparatus is needed for the reaction to be carried out under reduced pressure condition. Therefore, it is desirable to carry out the reaction under either pressurized or normal pressure conditions. Contact time is usually 0.1–300 seconds, and desirably 1–30 seconds.

The raw material for the hydrogen reduction reaction, 1,2-dichlorohexafluorocyclobutane, can be synthesized by carrying out a vapor phase dimerization reaction of 1,2,2-trifluoro-1-chloroethylene (chlorotrifluoroethylene) under pressurized conditions, particularly at a pressure of 2 kg/cm$^2$ or more, in a 200°–400° C. temperature range.

When this vapor phase dimerization of chlorotrifluoroethylene is carried out under normal pressure condition, the conversion is low at the reaction temperature of 500° C. or less. Moreover, at the reaction temperature of greater than 500° C., a lower range of the selectivity occurs due to the formation of acyclic compounds with 4 carbon atoms, therefore the reaction is not suitable as an industrial manufacturing method. However, when the reaction is carried out under pressurized conditions, 1,2-dichlorohexafluorocyclobutane can be synthesized with good conversion and high selectivity even at a reaction temperature of 400° C. or less.

Increasing in the pressure for the dimerization reaction the targeted 1,2-dichlorohexafluorocyclobutane can be obtained at a lower temperature with good conversion and high selectivity. When the reaction pressure is increased further, a reaction system durable enough to withstand high pressure is needed. Usually, therefore, it is usually better to carry out this reaction under a pressure of 2–20 kg/cm$^2$.

In this vapor phase dimerization reaction, decreasing in the flow rate of the raw material, chlorotrifluoroethylene, the conversion rate is increased. However, the conversion can also be increased by using an appropriate packing. Glass beads, nickel beads, globular silica or active carbon can be used as the packing.

INDUSTRIAL FEASIBILITY

According to the invention's method, hexafluorocyclobutene is manufactured by the dechlorination of 1,2-dichlorohexafluorocyclobutane using hydrogen in the presence of a catalyst consisting of metal oxide and/or silicon oxide. Therefore, 1,2-dichlorohexafluorocyclobutane, which can be available at a low price, can easily be converted to hexafluorocyclobutene in a single step with high selectivity. The hexafluorocyclobutene can be used as a raw material for detergents and HFC blowing agents which do not contribute to the depletion of the ozone layer. The compound is also useful as a raw material for various resins, and as an intermediate for medicinal drugs and agricultural chemicals.

Moreover, since (Z)-1,2,3,3,4,4-hexafluorocyclobutane is manufactured by carrying out a hydrogen reduction of hexafluorocyclobutene using the vapor phase method in the presence of a palladium catalyst, the target substance can be obtained with high selectivity. The (Z)-1,2,3,3,4,4-hexafluorocyclobutane is useful as an alternate for the CFCs and HCFCs used as refrigerants, blowing agents, and detergents.

In addition, (Z)-1,2,3,3,4,4-hexafluorocyclobutane can be manufactured with a high yield by carrying out the hydrogen-adding reaction (hydrogen reduction) using the raw material, 1-2-dichlorohexafluorocyclobutane, in the presence of a rhodium catalyst.

EMBODIMENT

The invention will be explained in details with reference to the below examples.

ACTUAL OPERATION EXAMPLE 1

120 g of Cr(NO$_3$)$_3$·9H$_2$O was dissolved in 250 ml of water. With stirring, this solution and 200 ml of a 28% ammonium hydroxide solution were added to 400 ml of heated water and the hydroxide precipitate was obtained. After the precipitate was filtered, washed with pure water, and dried, it was dried for five hours at 450° C. to obtain the oxide powder (chromium oxide). Using a tablet machine, the oxide powder was formed into cylindrical shapes 5 mm in diameter and 5 mm in height.

A reaction tube (diameter 20 mm×1000 mm) made of Hastelloy C was filled with 10 g of the chromium oxide catalyst described above and the reaction temperature was set.

Pretreatment of the reaction tube was performed by passing hydrogen through the tube for three hours at a flow rate of 200 ml/min. Afterwards, 1,2-dichlorohexafluorocyclobutane was passed through the tube at a flow rate of 50 ml/min in addition to the hydrogen flow.

After the produced gas was washed with water, it was analyzed by gas chromatography. The selectivity and the conversion were calculated by multiplying the correction coefficient, which was independently determined, by the gas chromatography peak areas. Table 1 shows the results.

TABLE 1

| Reaction temperature | Conversion | Selectivity |
|---|---|---|
| 300° C. | 25% | 86% |
| 350° C. | 47% | 85% |
| 400° C. | 76% | 84% |

The main by-product was tetrafluoro-1-chlorocyclobutene. However, we found that the targeted hexafluorocyclobutene (1,2,3,3,4,4-hexafluoro-1-cyclobutene) could be synthesized with good conversion and high selectivity.

ACTUAL OPERATION EXAMPLE 2

We carried out another reaction in the same manner as that shown in actual operation example 1, but used compound oxide of copper oxide and chromia as the catalyst. Table 2 shows the results. We found that the targeted hexafluorocyclobutene could be synthesized with good conversion and high selectivity.

TABLE 2

| Reaction temperature | Conversion | Selectivity |
|---|---|---|
| 300° C. | 35% | 77% |
| 350° C. | 56% | 75% |
| 400° C. | 77% | 72% |

ACTUAL OPERATION EXAMPLE 3

We carried out another reaction in the same manner as that shown in actual operation example 1, but used iron oxide as the catalyst. Table 3 shows the results.

TABLE 3

| Reaction temperature | Conversion | Selectivity |
|---|---|---|
| 300° C. | 21% | 79% |
| 350° C. | 36% | 76% |
| 400° C. | 71% | 68% |

The main by-product was tetrafluoro-1-chlorocyclobutene. However, we found that the targeted hexafluorocyclobutene could be synthesized with good conversion and high selectivity.

ACTUAL OPERATION EXAMPLE 4

87 g of Ni $(NO_3)_2 \cdot 6H_2O$ was dissolved in 250 ml of water, and 181 g of silica gel was added to the solution, and the mixture was dried. The residue was then heated at 400° C. and nickel oxide catalyst was obtained. Using a tablet machine, the nickel oxide catalyst was formed into cylindrical shapes 5 mm in diameter and 5 mm in height.

A reaction tube (diameter 20 mm×1000 mm) made of Hastelloy C was filled with 10 g of the nickel oxide catalyst described above (the carrier was silica gel) and the reaction temperature was set.

Pretreatment of the reaction tube was then performed by passing hydrogen through the tube for three hours at a flow rate of 200 ml/min. Afterwards, 1,2-dichlorohexafluorocyclobutane was passed through the tube at a flow rate of 50 ml/min in addition to the hydrogen flow.

After the produced gas was washed with water, it was analyzed by gas chromatography. The selectivity and the conversion were calculated by multiplying the correction coefficient, which was independently determined, by the gas chromatography peak areas. Table 4 shows the results.

TABLE 4

| Reaction temperature | Conversion | Selectivity |
|---|---|---|
| 300° C. | 22% | 82% |
| 350° C. | 46% | 75% |
| 400° C. | 75% | 72% |

The main by-product was tetrafluoro-1-chlorocyclobutene. However, we found that the targeted hexafluorocyclobutene could be synthesized with good conversion and high selectivity.

ACTUAL OPERATION EXAMPLE 5

120 g of Cr $(NO_3)_3 \cdot 9H_2O$ was dissolved in 250 ml of water, and 181 g of silica gel was added to the solution, and the mixture was dried. The mixture was then heated at 400° C. and chromium oxide catalyst was obtained. Using a tablet machine, the chromium oxide catalyst was formed into cylindrical shapes 5 mm in diameter and 5 mm in height.

A reaction tube (diameter 20 mm×1000 mm) made of Hastelloy C was filled with 10 g of the chromium oxide catalyst described above (the carrier was silica gel) and the reaction temperature was set.

Pretreatment of the reaction tube was performed done by passing hydrogen through the tube for three hours at a flow rate of 200 ml/min. Afterwards, 1,2-dichlorohexafluorocyclobutane was passed through the tube at a flow rate of 50 ml/min in addition to the hydrogen flow.

After the produced gas was washed with water, it was analyzed by gas chromatography. The selectivity and the conversion were calculated by multiplying the correction coefficient, which was independently determined, by the gas chromatography peak areas. Table 5 shows the results.

TABLE 5

| Reaction temperature | Conversion | Selectivity |
|---|---|---|
| 300° C. | 24% | 88% |
| 350° C. | 50% | 86% |
| 400° C. | 81% | 85% |

The main by-product was tetrafluoro-1-chlorocyclobutene. However, we found that the targeted hexafluorocyclobutene could be synthesized with good conversion and high selectivity.

ACTUAL OPERATION EXAMPLE 6

A solution of potassium fluoride (5.4 mol) was added to a solution of calcium nitrate (2.7 mol), and copper nitrate (1 mol), nickel nitrate (1 mol), and chromium nitrate (1 mol), were added to the slurry. Potassium hydroxide (0.1 mol) was then added. The precipitate was filtered and dried, then heated at 400° C. to produce the mixed oxide. Using a tablet machine, the oxide was formed into cylindrical shapes 5 mm in diameter and 5 mm in height.

A reaction tube (diameter 20 mm×1000 mm) made of Hastelloy C was filled with 10 g of the catalyst described above (the carrier was calcium fluoride) and the reaction temperature was set.

Pretreatment of the reaction tube was performed by passing hydrogen through the tube for three hours at a flow rate of 200 ml/min. Afterwards, 1,2-dichlorohexafluorocyclobutane was passed through the tube at a flow rate of 50 ml/min in addition to the hydrogen flow.

After the produced gas was washed with water, it was analyzed by gas chromatography. The selectivity and the conversion were calculated by multiplying the correction coefficient, which was independently determined by the gas chromatography peak areas. Table 6 shows the results.

TABLE 6

| Reaction temperature | Conversion | Selectivity |
|---|---|---|
| 300° C. | 35% | 89% |
| 350° C. | 85% | 78% |
| 400° C. | 93% | 75% |

The main by-product was tetrafluoro-1-chlorocyclobutene. However, we found that the targeted hexafluorocyclobutene could be synthesized with good conversion and high selectivity.

ACTUAL OPERATION EXAMPLE 7

A reaction tube (diameter 20 mm×1000 mm) made of Hastelloy C was filled with 10 g of CARiACT-30 (manufactured by Fuji Davison Co.,Ltd.). Nitrogen was passed through the tube at a flow rate of 40 cc/min at 400° C. for three hours.

Afterwards, the flow of nitrogen was stopped and hydrogen was passed through at the same temperature at a flow rate of 30 cc/min, and then, additional 1,2- dichlorohexafluorocyclobutane was passed through at a flow rate of 6 cc/min. After the produced gas was washed with water, it was analyzed by gas chromatography.

The conversion of 1,2-dichlorohexafluorocyclobutane was 30%, the selectivity of the targeted hexafluorocyclobutene was 96% and a 3.5% selectivity of tetrafluoro-1-chlorocyclobutene was formed as the by-product. The selectivity and the conversion were calculated by multiplying the correction coefficient, which was independently determined by the gas chromatography peak areas. The same procedure was used for the following operations.

ACTUAL OPERATION EXAMPLE 8

Based on actual operation example 7, the flow rates for each raw material and reaction temperature were changed. The hydrogen flow rate was set at 30 cc/min. and the flow rate for 1,2-dichlorohexafluorocyclobutane was changed to 3 cc/min. The reaction temperature was changed to 450° C. and the another reaction conditions were the same manner as in actual operation example 7.

The converion for 1,2-dichlorohexafluorocyclobutane was 45%, the selectivity or the targeted hexafluorocyclobutene was 94% and a 5.3% selectivity of tetrafluoro-1-chlorocyclobutene was formed as the by-product.

ACTUAL OPERATION EXAMPLE 9

Based on actual operation example 7, Silbead (manufactured by Mizusawa Chemical Industry Co., Ltd.) was substituted as the catalyst and the reaction was carried out in the same manner as in actual operation example 7 except for the catalyst.

The conversion for 1,2-dichlorohexafluorocyclobutane was 22%, the selectivity of the targeted hexafluorocyclobutene was 94% and a 5.3% selectivity of tetrafluoro-1-chlorocyclobutene was formed as the by-product.

ACTUAL OPERATION EXAMPLE 10

A reaction tube made of SUS316 with an inner diameter of 7 mm and a length of 150 mm was filled with 4.6 cc of palladium catalyst supported at 3% concentration on active carbon. The reaction tube was heated to 100° C. using an electric furnace while a flow of nitrogen gas was passed. After the tube reached the designated temperature, hexafluorocyclobutene was introduced at a flow rate of 2.0 cc/min together with hydrogen at a flow rate of 10 cc/min. The reaction temperature was maintained at 100° C.

After the produced gas was washed with water, it was analyzed by gas chromatography. Table 7 shows the results.

ACTUAL OPERATION EXAMPLE 11

A reaction tube identical to that used in actual operation example 10 was filled with 4.6 cc of palladium catalyst supported at 3% concentration on active carbon. The reaction tube was heated to 80° C. using an electric furnace while a flow of nitrogen gas was passed. After the tube reached the designated temperature, hexafluorocyclobutene was introduced at a flow rate of 8.0 cc/min together with hydrogen at a flow rate of 40 cc/min. The reaction temperature was maintained at 80° C.

After the produced gas was washed with water, it was analyzed by gas chromatography. Table 7 shows the results.

ACTUAL OPERATION EXAMPLE 12

A reaction tube identical to that used in actual operation example 10 was filled with 2.3 cc of palladium catalyst supported at 0.5% concentration on active carbon. A flow of nitrogen gas was passed through the tube at room temperature. Afterwards, hexafluorocyclobutene was introduced at a flow rate of 5 cc/min together with hydrogen at a flow rate of 10 cc/min. The reaction temperature was maintained at 27° C.

After the gas produced was washed with water, it was analyzed by gas chromatography. Table 7 shows the results.

ACTUAL OPERATION EXAMPLE 13

A reaction tube identical to that used in actual operation example 10 was filled with 1.9 cc of palladium catalyst supported at 0.5% concentration on alumina. The reaction tube was heated to 100° C. using an electric furnace while a flow of nitrogen gas was passed. After the tube reached the designated temperature, hexafluorocyclobutene was introduced at a flow rate of 5 cc/min together with hydrogen at a flow rate of 15 cc/min. The reaction temperature was maintained at 100° C.

After the produced gas was washed with water, it was analyzed by gas chromatography. Table 7 shows the results.

TABLE 7

| Actual operation example | Conversion (%) | Selectivity (%) |
| --- | --- | --- |
| Example 10 | 100 | 97.7 |
| Example 11 | 98.7 | 99.1 |
| Example 12 | 82 | 100 |
| Example 13 | 100 | 86.5 |

The main by-product was tetrafluoro-1-chlorocyclobutene. However, we found that the targeted (Z)-1,2,3,3,4,4-hexafluorocyclobutane could be synthesized with good conversion and high selectivity.

ACTUAL OPERATION EXAMPLE 14

A reaction tube made of SUS316 with an inner diameter of 7 mm and a length of 150 mm was filled with 1 g of rhodium catalyst supported at 0.5% concentration on active carbon. The reaction tube was heated to 225° C. using an electric furnace while a flow or nitrogen gas was passed. After the tube reached the designated temperature, 1,2-dichlorohexafluorocyclobutane was introduced at a flow rate of 1.1 ml/min together with hydrogen at a flow rate of 10.0 ml/min. The reaction temperature was maintained at 225° C. After the produced gas was washed with water, it was analyzed by gas chromatography. Table 8 shows the results.

ACTUAL OPERATION EXAMPLE 15

A reaction tube same to that used in actual operation example 14 was filled with 1 g of rhodium catalyst supported at 3% concentration on active carbon. The reaction tube was heated to 225° C. using an electric furnace while a flow of nitrogen gas was passed. After the tube reached the designated temperature, 1,2-dichlorohexafluorocyclobutane was introduced at a flow rate of 1.4 ml/min together with hydrogen at a flow rate of 10.0 ml/min. The reaction temperature was maintained at 225° C. After the produced gas was washed with water, it was analyzed by gas chromatography. Table 8 shows the results.

ACTUAL OPERATION EXAMPLE 16

A reaction tube same to that used in actual operation example 14 was filled with 1 g of rhodium catalyst supported at 3% concentration on active carbon. The reaction tube was heated to 250° C. using an electric furnace while a flow of nitrogen gas was passed. After the tube reached the designated temperature, 1,2-dichlorohexafluorocyclobutane was introduced at a flow rate of 1.5 ml/min together with hydrogen at a flow rate of 10.0 ml/min. The reaction temperature was maintained at 250° C. After the produced gas was washed with water, it was analyzed by gas chromatography. Table 8 shows the results.

ACTUAL OPERATION EXAMPLE 17

A reaction tube same to that used in actual operation example 14 was filled with 1 g of rhodium catalyst supported at 3% concentration on active carbon. The reaction tube was heated to 150° C. using an electric furnace while a flow of nitrogen gas was passed. After the tube reached the designated temperature, 1,2-dichlorohexafluorocyclobutane was introduced at a flow rate of 1.5 ml/min together with hydrogen at a flow rate of 10.0 ml/min. The reaction temperature was maintained at 150° C. After the produced gas was washed with water, it was analyzed by gas chromatography. Table 8 shows the results.

COMPARISON EXAMPLE 1

A reaction tube same to that used in actual operation example 14 was filled with 1 g of palladium catalyst supported at 0.5% concentration on active carbon. The reaction tube was heated to 200° C. using an electric furnace while a flow of nitrogen gas was passed. After the tube reached the designated temperature, 1,2-dichlorohexafluorocyclobutane was introduced at a flow rate of 1.7 ml/min together with hydrogen at a flow rate of 10.0 ml/min. The reaction temperature was maintained at 200° C. After the produced gas was washed with water, it was analyzed by gas chromatography. Table 8 shows the results.

COMPARISON EXAMPLE 2

A reaction tube same to that used in actual operation example 14 was filled with 1 g of platinum catalyst supported at 0.5% concentration on active carbon. The reaction tube was heated to 150° C. using an electric furnace while a flow of nitrogen gas was passed. After the tube reached the designated temperature, 1,2-dichlorohexafluorocyclobutane was introduced at a flow rate of 1.4 ml/min together with hydrogen at a flow rate of 10.0 ml/min. The reaction temperature was maintained at 150° C. After the produced gas was washed with water, it was analyzed by gas chromatography. Table 8 shows the results.

TABLE 8

| Actual operation example | Conversion (%) | Selectivity (%) |
| --- | --- | --- |
| Example 14 | 100 | 92 |
| Example 15 | 98 | 95 |
| Example 16 | 100 | 93 |
| Example 17 | 66 | 94 |
| Comparison example 1 | 88 | 30 |
| Comparison example 2 | 68 | 51 |

We found that by employing the methods based on the invention, the targeted (Z)-1,2,3,3,4,4-hexafluorocyclobutane could be synthesized with good conversion and high selectivity depending on the temperature.

ACTUAL OPERATION EXAMPLE 18

A reaction tube made of SUS316 with an inner diameter of 2 cm and a length of 40 cm was filled with 20 ml of glass beads with diameters of approximately 1 mm. Using a back pressure regulating valve, the inner pressure of the tube was regulated at 2 kg/cm$^2$. The tube was heated to 300° C. using an electric furnace while a flow of nitrogen gas was passed. After the tube reached the designated temperature, chlorotrifluoroethylene was introduced at a flow rate of 18 ml/min. The reaction temperature was maintained at 300° C. After the produced gas was washed with water, it was analyzed by gas chromatography. Table 9 shows the results.

ACTUAL OPERATION EXAMPLE 19

A reaction tube same to that used in actual operation example 18 was filled with 20 ml of glass beads with diameters of approximately 1 mm. Using a back pressure regulating valve, the inner pressure of the tube was regulated at 2 kg/cm$^2$. The reaction tube was heated to 400° C. using an electric furnace while a flow of nitrogen gas was passed. After the tube reached the designated temperature, chlorotrifluoroethylene was introduced at a flow rate of 18 ml/min. The reaction temperature was maintained at 400° C. After the produced gas was washed with water, it was analyzed by gas chromatography. Table 9 shows the results.

ACTUAL OPERATION EXAMPLE 20

A reaction tube same to that used in actual operation example 18 was filled with 20 ml of nickel beads with diameters of approximately 2 mm. Using a back pressure regulating valve, the inner pressure of the tube was regulated at 4 kg/cm$^2$. The reaction tube was heated to 350° C. using an electric furnace while a flow of nitrogen gas was passed. After the tube reached the designated temperature, chlorotrifluoroethylene was introduced at a flow rate of 75 ml/min. The reaction temperature was maintained at 350° C. After the produced gas was washed with water, it was analyzed by gas chromatography. Table 9 shows the results.

ACTUAL OPERATION EXAMPLE 21

A reaction tube same to that used in actual operation example 18 was filled with 20 ml of globular silica gel (CARiACT) with an average diameter of approximately 3 mm. Using a back pressure regulating valve, the inner pressure of the tube was regulated at 4 kg/cm$^2$. The reaction tube was heated to 350° C. using an electric furnace while a flow of nitrogen gas was passed. After the tube reached the designated temperature, chlorotrifluoroethylene was introduced at a flow rate of 75 ml/min. The reaction temperature was maintained at 350° C. After the produced gas was washed with water, it was analyzed by gas chromatography. Table 9 shows the results.

TABLE 9

| Actual operation example | Conversion (%) | Selectivity (%) |
| --- | --- | --- |
| Example 18 | 17 | 96 |
| Example 19 | 65 | 99 |
| Example 20 | 11 | 95 |
| Example 21 | 14 | 90 |

From these results, we found that the 1,2-dichlorohexafluorocyclobutane used as the raw material in Examples 14–17 can be obtained with high selectivity by carrying out the vapor phase chlorotrifluoroethylene dimerization reaction under pressurized conditions.

We claim:

1. A manufacturing method for hexafluorocyclobutene by dechlorinating 1,2-dichlorohexafluorobutane using hydrogen in the presence of a catalyst consisting of metal oxide and/or silicon oxide, the metal oxide catalyst comprising at least one metal selected from iron, chromium, cobalt, copper, and nickel.

2. A manufacturing method described in claim 1 in which the metal oxide catalyst is supported by a carrier comprising one or more substances selected from the group consisting of active carbon, alumina, aluminum fluoride, and calcium fluoride.

3. A manufacturing method described in one of claims 1 or 2 in which 1,2-dichlorohexafluorocyclobutane is dechlorinated employing at least a stoichiometric quantity of hydrogen.

4. A manufacturing method described in one of claims 1 or 3 in which dechlorination is carried out under a temperature range of 200°–500° C.

5. A manufacturing method described in one of claims 1 or 2 in which 1,2-dichlorohexafluorocyclobutane is obtained by a 1,2,2-trifluoro-1-chloroethylene dimerization reaction.

6. A method of manufacturing (Z)-1,2,3,3,4,4-hexafluorocyclobutane by dechlorinating 1,2-dichlorohexafluorobutane using hydrogen in the presence of a catalyst consisting of metal oxide and/or silicon oxide to obtain hexafluorocyclobutene, the metal oxide catalyst comprising at least one metal selected from iron, chromium, cobalt, copper, and nickel, and by performing vapor-phase hydrogen reduction of the hexafluorocyclobutene under conditions in which a palladium catalyst is present.

7. A manufacturing method described in claim 6 in which a palladium catalyst is supported by a carrier consisting of one or more substances selected from active carbon, alumina, silica gel, titanium oxide, and zirconia.

8. A manufacturing method described in claim 7 in which the carrier support concentration for the palladium catalyst is set at 0.05–10%.

9. A manufacturing method described in one of claims 6–8 in which the hydrogenation of hexafluorocyclobutene is carried out employing at least a stoichiometric quantity of hydrogen.

10. A manufacturing method described in one of claims 6–8 in which the hydrogen reduction reaction is carried out under a temperature range of 20°–300° C.

11. A manufacturing method described in one of claims 6–8 in which hexafluorocyclobutene is obtained by employing a manufacturing method described in one of claim 2.

12. A manufacturing method described in claim 11 in which the 1,2-dichlorohexafluorocyclobutane used to manufacture hexafluorocyclobutene is obtained by the 1,2,2-trifluoro-1-chloroethylene dimerization reaction.

13. A method of manufacturing (Z)-1,2,3,3,4,4-hexafluorocyclobutane by carrying out vapor-phase hydrogen reduction of 1,2-dichlorohexafluorocyclobutane in the presence of a rhodium catalyst.

14. A manufacturing method described in claim 13 in which the rhodium catalyst comprises rhodium supported by a carrier consisting of one or more substances selected from active carbon, alumina, silica, and zirconia.

15. A manufacturing method described in claim 14 in which the carrier support concentration for the rhodium catalyst is set at 0.05–10%.

16. A manufacturing method described in one of claims 13–15 in which 2–10 equivalents of hydrogen relative to the amount of 1,2-dichlorohexafluorocyclobutane are used.

17. A manufacturing method described in one of claims 13–15 in which the reaction is carried out under a temperature range of 150°–300° C.

18. A manufacturing method described in one of claims 13–15 in which 1,2-dichlorohexafluorocyclobutane is synthesized by carrying out the vapor-phase 1,2,2-trifluoro-1-chloroethylene dimerization reaction.

19. A manufacturing method described in claim 18 in which the dimerization reaction is carried out under a pressure range of 2–20 kg/cm².

20. A manufacturing method described in claim 18 or 19 in which the dimerization reaction is carried out under a temperature range of 200°–400° C.

* * * * *